US005895842A

United States Patent [19]

Henderson

[11] Patent Number: 5,895,842
[45] Date of Patent: Apr. 20, 1999

[54] ROBUST TRANSDUCER FOR VISCOELASTIC MEASUREMENT

[75] Inventor: Jon H. Henderson, Wheat Ridge, Colo.

[73] Assignee: Sienco, Inc., Wheat Ridge, Colo.

[21] Appl. No.: 08/863,107

[22] Filed: May 23, 1997

[51] Int. Cl.⁶ .......................... G01N 11/16; G01N 33/48
[52] U.S. Cl. ...................... 73/54.26; 73/64.42; 73/54.23
[58] Field of Search .......................... 73/54.26, 54.24, 73/64.42, 54.23, 54.25

[56] References Cited

U.S. PATENT DOCUMENTS

| | | | |
|---|---|---|---|
| 3,587,295 | 6/1971 | Simons | 73/64.1 |
| 3,712,117 | 1/1973 | Fitzgerald et al. | 73/59 |
| 3,722,262 | 3/1973 | Gilinson, Jr. et al. | 73/59 |
| 4,023,400 | 5/1977 | November | 73/54 |
| 4,026,671 | 5/1977 | Simons et al. | 23/259 |
| 4,148,216 | 4/1979 | Do et al. | 73/59 |
| 4,154,093 | 5/1979 | Smith et al. | 73/54 |
| 4,202,204 | 5/1980 | Hartert | 73/64.1 |
| 4,312,217 | 1/1982 | Hartert | 73/64.1 |
| 4,328,701 | 5/1982 | Mau-Tung et al. | 73/59 |
| 4,341,111 | 7/1982 | Husar | 73/64.1 |
| 4,388,824 | 6/1983 | Krone | 73/64.1 |
| 4,488,427 | 12/1984 | Matusik et al. | 73/59 |
| 4,627,272 | 12/1986 | Wright | 73/57 |
| 4,754,640 | 7/1988 | Fitzgerald et al. | 73/54 |
| 4,862,735 | 9/1989 | Williams et al. | 73/54 |
| 4,869,098 | 9/1989 | Haakana | 73/64.1 |
| 4,905,499 | 3/1990 | Miura et al. | 73/32 A |
| 4,909,068 | 3/1990 | Miura et al. | 73/32 A |
| 5,067,344 | 11/1991 | Fitzgerald et al. | 73/54 |
| 5,113,353 | 5/1992 | George | 364/508 |
| 5,138,872 | 8/1992 | Henderson | 73/64.41 |
| 5,157,962 | 10/1992 | Fitzgerald et al. | 73/54.24 |
| 5,571,952 | 11/1996 | Kauzlarich | 73/54.24 |
| 5,596,139 | 1/1997 | Miura et al. | 73/54.24 |

Primary Examiner—Hezron Williams
Assistant Examiner—J. David Wiggins
Attorney, Agent, or Firm—William E. Hein

[57] ABSTRACT

A transducer for use in a viscoelastic analyzer of the type in which a mechanical probe member is immersed in a fluid or gel and driven to impart a desired oscillating motion to such fluid or gel whose viscoelastic properties are to be determined including means for restricting motion of the probe member of the transducer in all directions except the direction of desired oscillating motion.

2 Claims, 6 Drawing Sheets

ROBUST TRANSDUCER FOR VISCOELASTIC MEASUREMENT

REFERENCE TO RELATED PATENTS

The invention described herein is related to U.S. Pat. Nos. 5,016,469 and 5,138,872, the subject matter of both of which is incorporated herein by reference.

BACKGROUND AND SUMMARY OF THE INVENTION

This invention relates generally to instrumentation for making viscoelastic measurements and, more particularly, to an improved vibratory viscoelastic transducer for measuring the viscoelastic characteristics of fluids and gels.

Vibratory viscosity and viscoelastic analyzers are well known in the prior art. These analyzers typically incorporate a mechanical probe member that is driven to move in an oscillating or periodic manner. They include some means for imparting motion to the probe member and means for monitoring the probe displacement or motion. Most designs incorporate electronic means for driving the mechanical probe and monitoring the probe motion. The moving probe is immersed within a fluid or gel being tested. The motion characteristics of the moving probe are affected by the viscous and viscoelastic properties of the material being tested. The change in motion characteristics of the probe in response to a test sample is monitored and processed by the analyzer to determine the viscoelastic properties of the test sample.

The components of the drive mechanism or circuit, the mechanical probe, and the motion detection mechanism collectively comprise a transducer. The transducer has response characteristics that relate the input drive signal to the output motion signal. The response of the transducer is dependent on its physical design and the viscoelastic properties of the material being tested. The transducer characteristics can be represented using mechanical or electrical performance properties. U.S. Pat. No. 4,341,111 to Husar employs mechanical displacement versus frequency to characterize transducer behavior. This type of characterization is illustrated in FIG. 6. From the perspective of the electrical design, it is often desirable to characterize the transducer behavior in terms of electrical impedance. FIG. 5 illustrates the change in electrical impedance versus frequency for a viscoelastic transducer like that shown in FIGS. 1 and 2. This type of transducer monitors probe velocity rather than probe displacement. Both displacement and velocity monitoring transducers are nonlinear with respect to drive frequency and typically exhibit a pronounced peak at the natural resonant frequency. This resonant frequency varies in response to the viscoelastic properties of the liquid or gel being measured. These peaks are present in the examples illustrated in FIGS. 5 and 6.

Viscoelastic transducers vary widely in their design. One variation relates to the direction of probe motion. Prior art designs have incorporated axial, lateral, orbital or radial probe motion within the transducer. Exemplary of prior art transducers that employ an axially vibrating probe are those described in U.S. Pat. Nos. 3,587,295 and 3,741,002 to Simons, as well as U.S. Pat. No. 4,026,671 to Simons et al. U.S. Pat. No. 4,312,217 to Hartert and U.S. Pat. No. 4,341,111 to Husar teach the use of an elastic rod driven to produce either lateral or orbital motion. U.S. Pat. No. 4,488,427 to Matusik et al. teaches rotational or radial mechanical oscillation. These prior art transducers incorporate a single flexible member that deforms to produce the desired mechanical motion. The axial vibrating transducer taught by the Simons and Simons et al. patents incorporates a diaphragm. The lateral or orbital motion taught by Hartert and Husar is achieved by employing an elastic rod driven so as to bend the rod in one direction for lateral motion or in two directions for orbital motion. The radial motion taught by Mutasik et al. is produced by employing an elastic cylindrical tube driven with a torsion force producing radial deflection.

Most vibratory transduces employ separate drive and pickup coils. However, the separate coils are not required. The transducer taught by Simons et al. incorporates a single coil used simultaneously for driving the transducer and for monitoring mechanical motion.

Viscosity or viscoelastic analyzers monitor the transducer response using suitable circuitry and possibly computational techniques to determine the viscous or viscoelastic properties of the material being tested. The circuitry for driving vibratory transducers is well known in the art and typically consist of a driving circuit to produce the oscillating mechanical motion and a monitoring circuit to monitor the mechanical motion. Additional circuitry, including means to regulate mechanical motion, monitor energy consumption, or condition signals for display is also taught in the prior art. Early designs drive the transducer at fixed frequencies. Later designs typically drive the transducer at the resonant frequency of the transducer immersed within the material being tested. In the later devices, the viscoelastic properties of the material under test are determined by analyzing only the resonant point of the vibrating transducer. The attenuation of the resonant peak characterizes the viscous property of the test sample, while the change in frequency characterizes its elastic property.

The accuracy of viscosity and viscoelastic measurement devices incorporating vibratory transducers is limited by the performance characteristics of the vibratory transducer. Prior art vibratory transducers are prone to poor manufacturing reproducibility, poor oscillation characteristics, temperature drift, long term drift, and humidity drift. Additionally, the durability of these transducers is lacking. Damage from operator handling can cause either transducer drift or failure. In some designs, the transducer moving coil can be pushed against a magnet or magnet pole, thereby potentially damaging the coil. In other designs, the transducer alignment can be compromised by minor operator mishandling, thereby causing transducer drift or impeding transducer oscillation.

None of the prior art transducers have specifically addressed the need for protecting the oscillating mechanical component from excessive applied force. While the transducer of Simons oscillated axially, the operator could cause lateral or excessive axial movement of the diapragm while mounting or removing a disposable probe. This excessive movement could result in the coil contacting either the magnet or magnet pole and thus damaging the coil. Approximately 95% of all service requirements for this design have involved damaged coils. Additionally, the transducer characteristics were prone to change if the diaphragm was stressed by excessive axial movement.

Summarizing the prior art, the oscillating transducer taught in U.S. Pat. No. 4,341,111 to Husar relys on lateral or orbital movement of an elastic rod. However, this reference does not address protecting the elastic rod from excessive deformation. The transducer taught in U.S. Pat. No. 4,488,427 to Matusik et al. involves a tube that is subjected to rotational deflection and in which alignment of the transducer requires that the tube be prevented from deflecting laterally. However, this reference does not address protecting the rotational tube from undesired lateral deflection. Similarly, the oscillating transducers taught in U.S. Pat. Nos. 4,154,093 and 4,869,098 have no provision for mechanical protection against excessive transducer displacement.

It is therefore a principal object of the present invention to provide a vibratory transducer that minimizes operator handling damage by providing mechanical stops that limit the elastic deformation of the mechanical probe and embody a mechanical probe design that is substantially rigid except in the desired elastic direction of motion.

This and other objects are accomplished in accordance with the illustrated preferred embodiment of the present invention by providing a circular spring assembly coaxially mounted to a mechanical probe to restrict motion of the probe member in all directions except the desired direction along the axis of the probe and by providing mechanical stops for limiting the range of desired motion along the axis of the probe.

DETAILED DESCRIPTION OF THE PREFERRED EMBODIMENT

Figure 1:
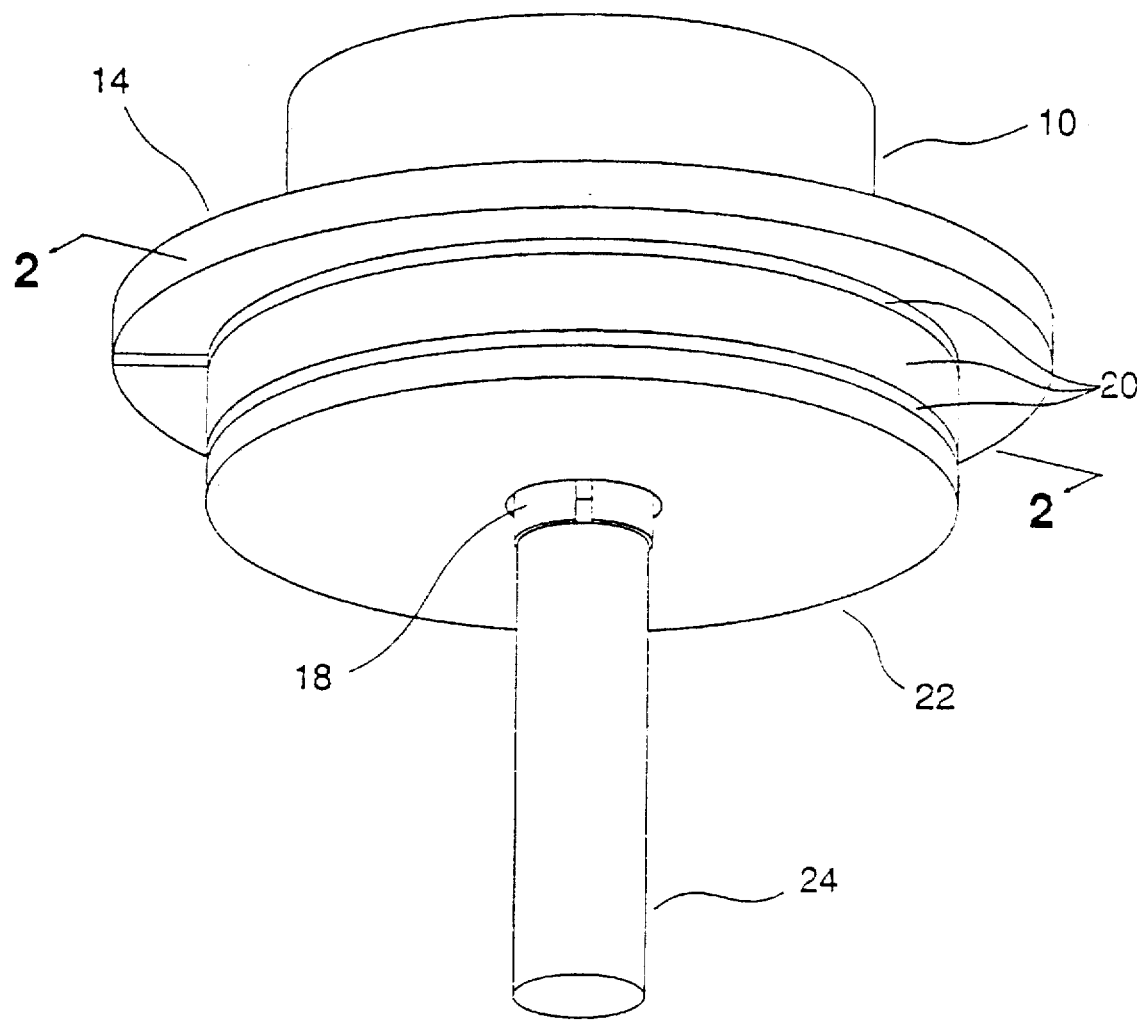
FIG. 1 is an overall pictorial diagram of a viscoelastic transducer constructed in accordance with the present invention.
Figure 2:
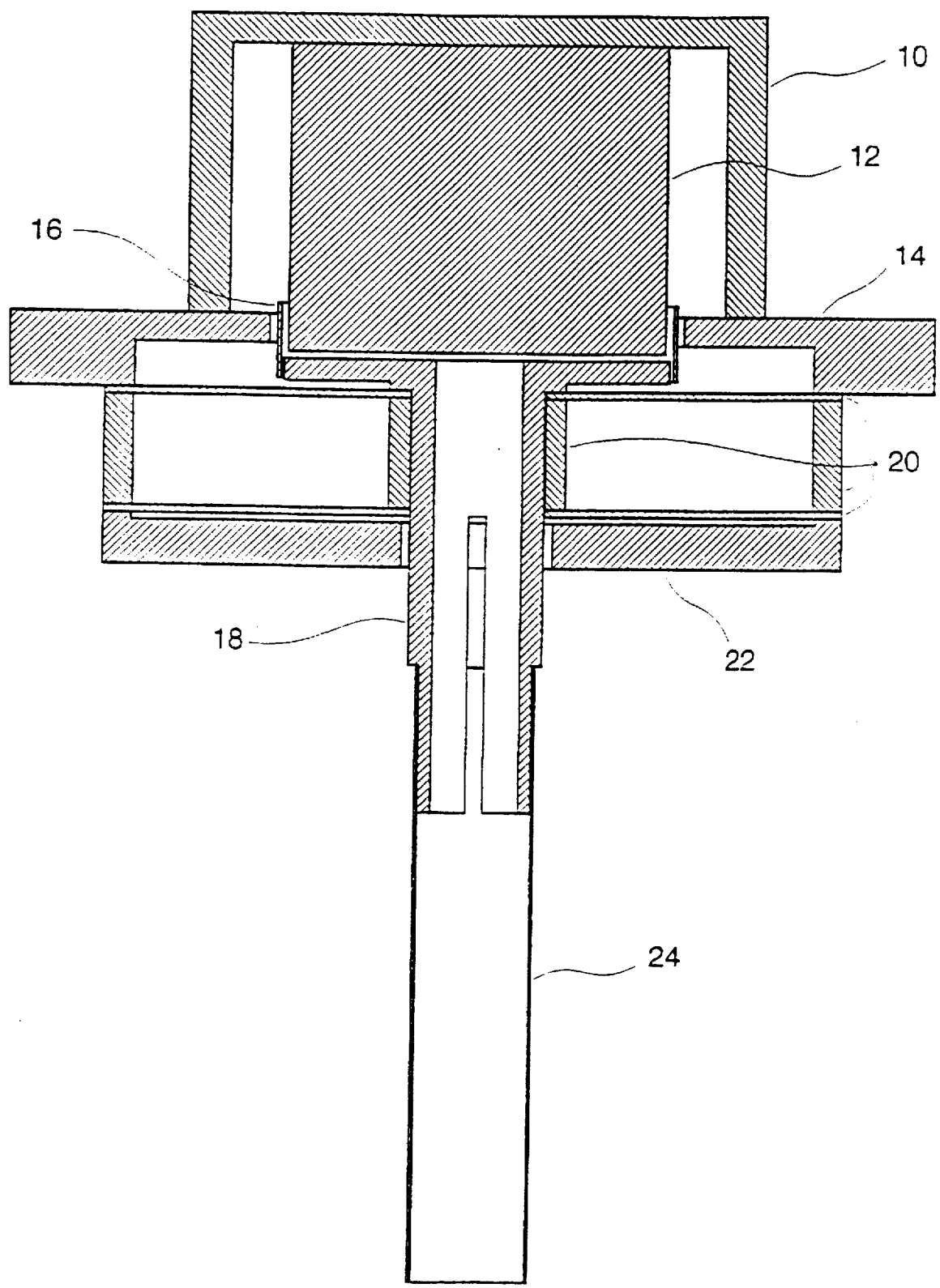
FIG. 2 is a diagram in cross section of the viscoelastic transducer of FIG. 1.
Figure 3:
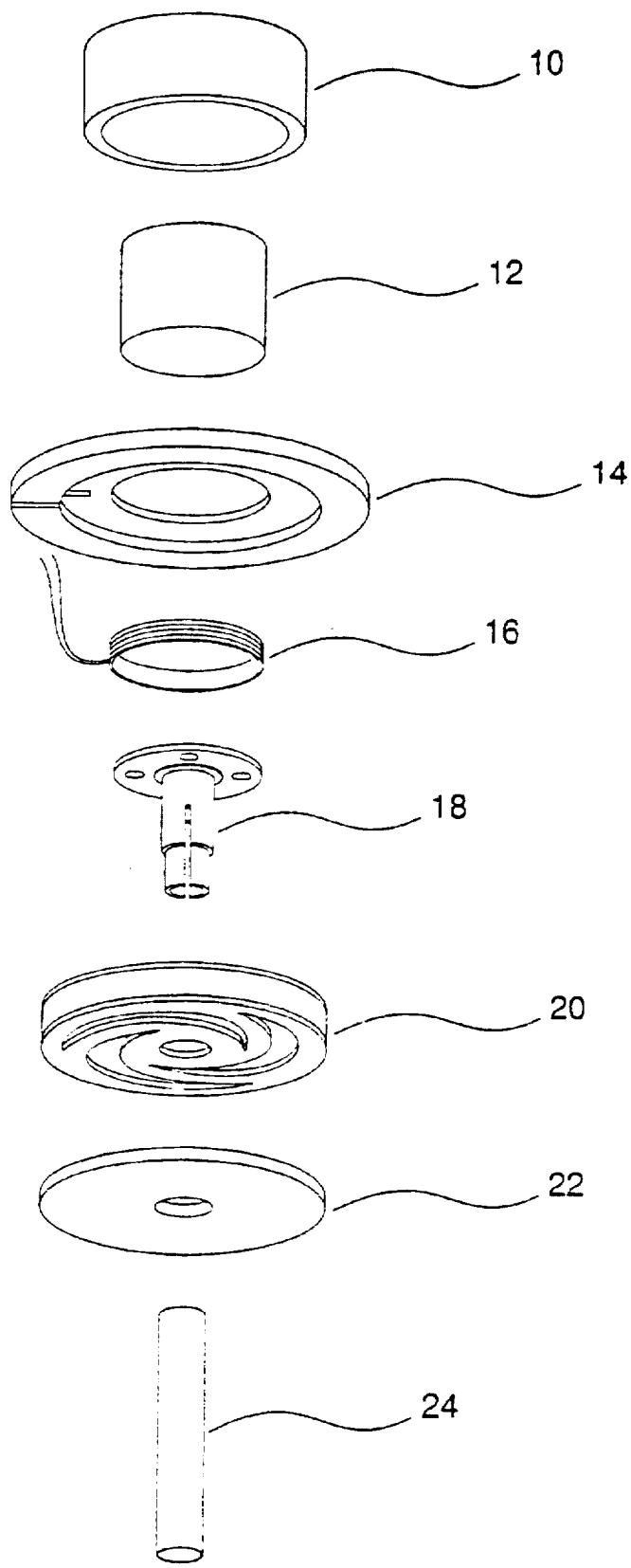
FIG. 3 is an exploded diagram of the viscoelastic transducer of FIGS. 1 and 2.

The viscoelastic transducer of the present invention may, for example, serve as a replacement for the transducer described in U.S. Pat. No. 5,016,469 to Henderson. The electronic circuitry described in that patent may be employed with the viscoelastic transducer of the present invention.

Referring now to FIGS. 1–4, there are shown a magnet cup 10, a permanent magnet 12, and magnet pole 14, aligned and adhesively assembled to produce a uniform magnetic field across the gap between permanent magnet 12 and magnet pole 14. A probe adapter hub 18 is adhesively attached to both a free-standing coil 16 and an inner ring 30 of a circular spring assembly 20. The outer rim of circular spring assembly 20 is aligned to position coil 11 within the gap between magnet 12 and pole 14 and is adhesively bonded to pole 14. Cover 22 is attached to the outer edge of the spring assembly 20 by means of an adhesive.

A mechanical probe that moves within the transducer of FIGS. 1–4 consists of a probe adapter hub 18, a coil 16, a disposable probe 24, and inner ring 30 of circular spring assembly 20. With proper alignment during assembly, the mechanical probe can move axially while maintaining clearance across the magnetic gap. Coil 16 is employed for driving the mechanical probe and for detecting probe motion.

Figure 5:
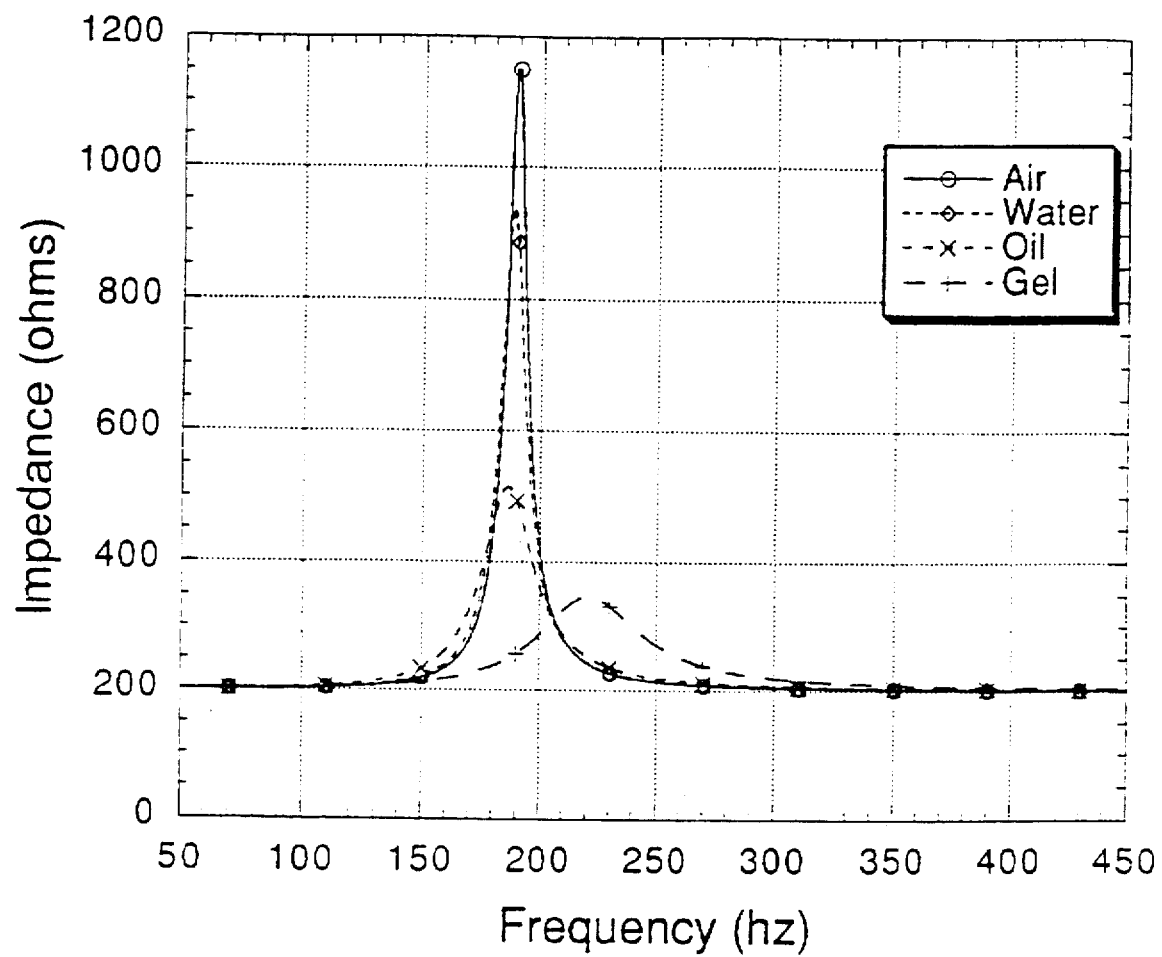
FIG. 5 is a graph that relates mechanical probe displacement to drive frequency for the viscoelastic transducer of FIGS. 1–4.
Figure 6:
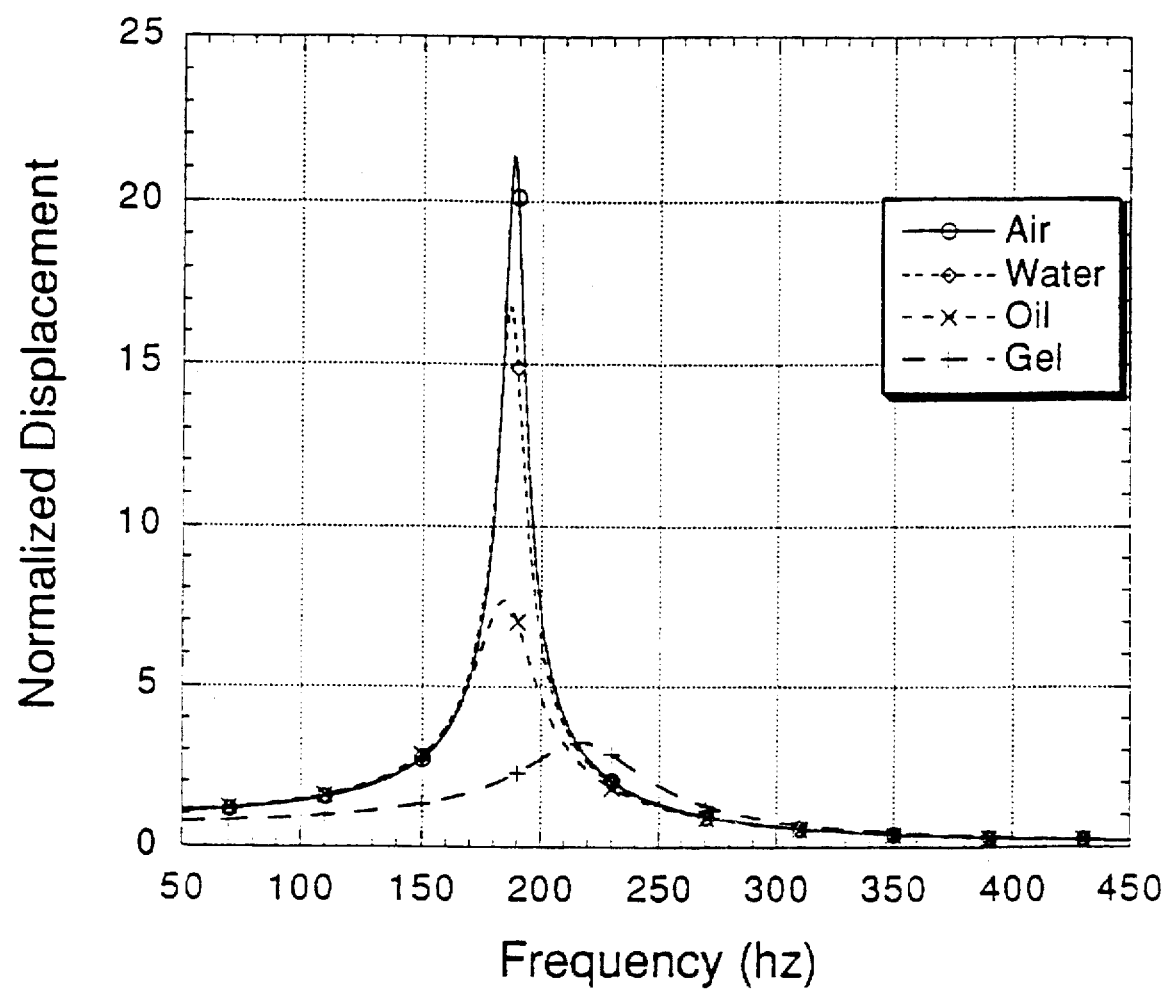
FIG. 6 is a graph that relates mechanical probe velocity to drive frequency for the viscoelastic transducer of FIGS. 1–4.

The typical characteristic response of the present transducer is illustrated in FIG. 5. This transducer can be used with a variety of conventional control circuits, but has been designed specifically for use with the circuitry described in U.S. Pat. No. 5,138,872. This circuitry serves to drive the transducer at the resonant frequency of the transducer moving within the test sample. The impedance of the transducer decreases with increasing viscosity. The resonant frequency increases with increasing elasticity. FIG. 5 illustrates the performance of the transducer in air, water, a heavy mineral oil, and a mineral oil gel. The attenuation of the resonant peak characterizes the viscous property of the test sample. The change in frequency characterizes the elastic property of the sample.

Figure 4:
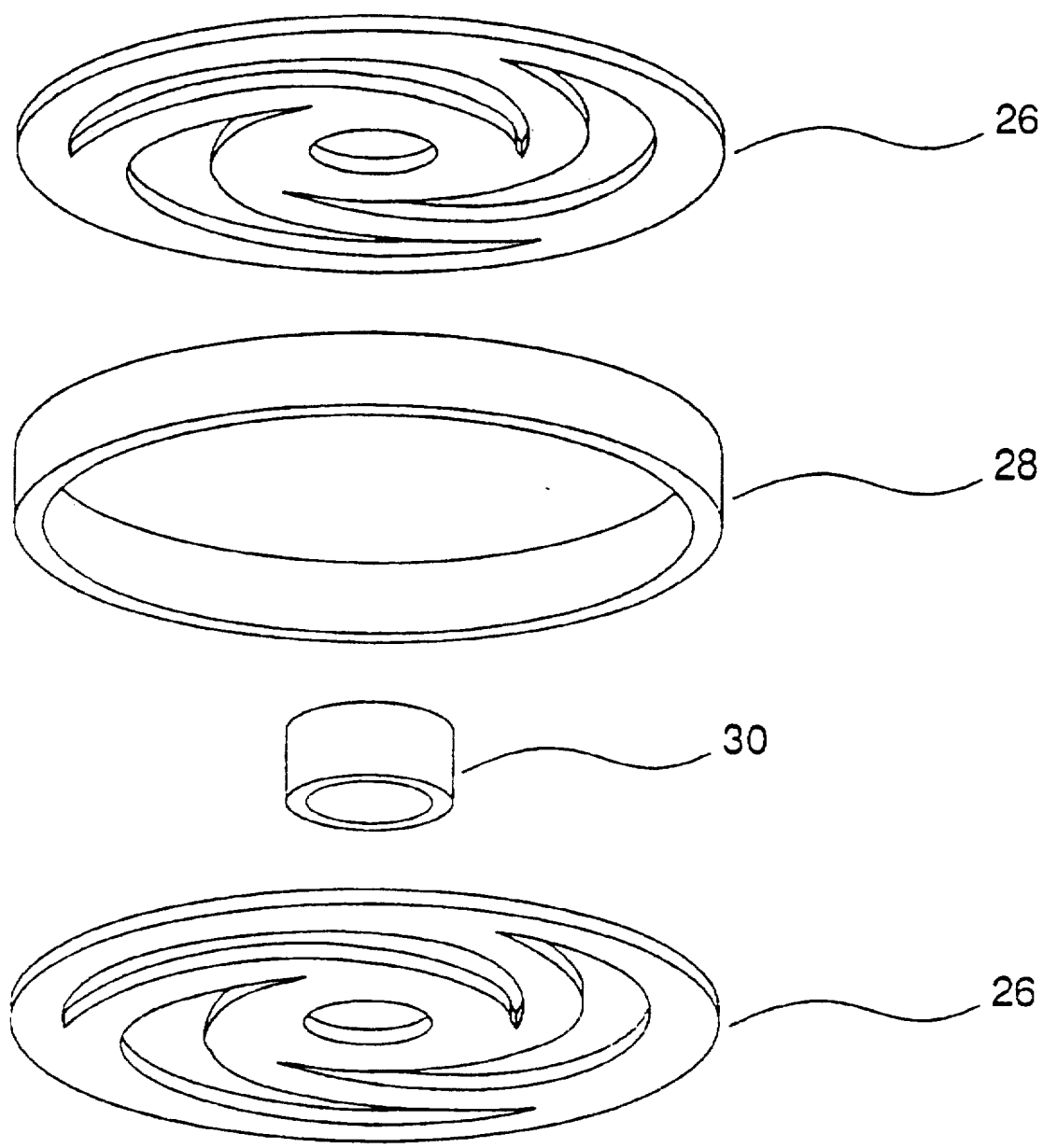
FIG. 4 is an exploded diagram of the circular spring assembly employed in the viscoelastic transducer of FIGS. 1–3.

Referring now more specifically to FIG. 4, it may be seen that circular spring assembly 20 is constructed from two circular springs 26 soldered to brass inner ring 30 and outer ring 28. The two circular springs 26 are constructed from beryllium copper sheet using a conventional photochemical machining process, such as that available through Conard Corporation of Glastonbury, Conn. The compliance of the two circular springs 26 may be varied by changing the length, width, or thickness of the spring webs. Materials other than beryllium copper may be used. However, beryllium copper is preferred because of its excellent and stable spring properties. The circular spring assembly 20 is preferably bonded using lead-tin solder, but could be welded, brazed, or glued.

As stated above, circular spring assembly 20 is constructed using two parallel springs 26 to provide lateral rigidity to mechanical probe. Use of a single spring would provide good performance as a viscoelastic transducer, but would not provide lateral rigidity to protect coil 16 from damage during operator handling associated with mounting or removing the disposable test probe. Spring assembly 20 provides rigidity in all directions of movement except axial displacement. More than two circular springs 26 could also be used. However, this wound add cost and complexity with only slight improvement in mechanical rigidity to withstand undesired mechanical deflections.

The mechanical design of the present viscoelastic transducer includes physical stops that limit the range of motion of the disposable mechanical probe 24. Magnet 12 limits inward deflection. Cover 22 limits outward deflection. These physical stops protect circular spring assembly 20 from excessive deformation when disposable probe 24 is mounted or removed. The design allows only about 0.010" of motion from the natural position of the probe adapter hub 18 to either magnet 12 or cover 22. This amount of motion is well within the elastic deflection operating region for circular spring assembly 20. However, these stops are located far beyond the approximate 0.00020" range of motion of the mechanical probe 24 during normal test operation.

In summary, the viscoelastic transducer of the present invention provides a simple, reliable, and accurate transducer for characterizing the viscoelastic properties of liquids and gels. Further, it improves upon the prior art by incorporating features to enhance the durability of the transducer against undesired mechanical stress and to limit mechanical deflection of the transducer to within the elastic operating limits of the spring member. This design also results in allowing spring assembly 20 to be very compliant without sacificing durability. High spring compliancy is desirable in improving the transducer sensitivity to weak gels.

While the present transducer has been described as an axial movement design, it could just as well be arranged for radial, lateral, orbital or any other type of oscillating motion.

The present transducer has been described as encompassing a single coil for both mechanical drive and motion pickup. However, separate coils could also be employed. Additional coils or other means could also be incorporated to permit additional degrees of movement. An orbital design may utilize multiple coils for drive and multiple coils for pickup. Drive and pickup devices should not be limited to include only coils. Other potential approaches could include Hall effect, capacitive, piezoelectric, or other forms of electromechanical energy conversion or detection.

Finally, the present transducer has been described as utilizing two flat circular springs to allow desired mechanical motion of the oscillating mechanical components. However, the invention is not limited to designs utilizing flat circular springs. An elastic member or members of many shapes including but not limited to coil springs, elastic tubes, deflecting rods, or wire could provide the elastic component for mechanical oscillation. Additionally, the mechanical oscillation does not require a mechanical elastic member if other mechanical oscillation via mechanical or electrical means is embodied.

I claim:

1. A transducer for use in a viscoelastic analyzer of the type in which a mechanical probe member is immersed in a fluid or gel whose viscoelastic characteristics are to be determined, the probe member being driven to impart a desired oscillating motion thereto, the improvement comprising means for restricting motion of the probe member in any direction except the direction of the desired oscillating motion, said means for restricting motion comprising a circular planar spring assembly coupled to the probe member for restricting motion of the probe member in all directions except along the axis of the probe member, said planar circular spring assembly comprising a pair of planar circular springs spaced apart from each other and coaxially coupled at their peripheral edges to a circular ring.

2. A transducer as in claim 1, wherein each of the circular planar springs comprises a beryllium copper circular ring.

* * * * *